United States Patent [19]

Jeppesen et al.

[11] Patent Number: 5,246,935
[45] Date of Patent: Sep. 21, 1993

[54] PIPERAZINYL DERIVATIVES AND METHODS OF TREATING CENTRAL NERVOUS SYSTEM AILMENTS RELATING TO THE 5-HT$_2$ RECEPTOR SYSTEM

[75] Inventors: Lone Jeppesen, Virum; Marit Kristiansen, Soborg; John B. Hansen, Jyderup, all of Denmark

[73] Assignee: Novo Nordisk A/S, Bagsvaerd, Denmark

[21] Appl. No.: 744,556

[22] Filed: Aug. 13, 1991

[30] Foreign Application Priority Data

Aug. 24, 1990 [DK] Denmark ................. 2039/90

[51] Int. Cl.$^5$ .................. C07D 401/10; C07D 405/10; C07D 295/108; A61K 31/495
[52] U.S. Cl. ..................... 514/253; 514/254; 514/255; 544/363; 544/368; 544/377; 544/392; 544/393; 544/394
[58] Field of Search ........ 514/253, 255, 254; 544/363, 368, 392, 393, 394, 377

[56] References Cited

U.S. PATENT DOCUMENTS

| | | | |
|---|---|---|---|
| 2,836,595 | 5/1958 | Parcell | 544/393 |
| 3,138,597 | 6/1964 | Schut | 544/393 |
| 4,202,898 | 5/1980 | Depoortere | 514/255 |
| 4,882,432 | 11/1989 | Abou-Gharbia et al. | 544/295 |
| 4,940,711 | 7/1990 | Nardi et al. | 514/255 |
| 5,143,916 | 9/1992 | Lavielle et al. | 544/392 |

FOREIGN PATENT DOCUMENTS

| | | | |
|---|---|---|---|
| 683208 | 3/1964 | Canada | 544/393 |
| 0015615 | 9/1980 | European Pat. Off. | |
| 0402644 | 12/1990 | European Pat. Off. | |
| 952142 | 3/1964 | United Kingdom | 544/393 |

OTHER PUBLICATIONS

Hayao et al., *J. Med. Chem.*, 6, pp. 133–135 (1963).
Hayao et al., *Chemical Abstracts*, vol. 58, No. 11358–11359 (1963).
Synthelabo Chemical Abstracts, vol. 93, No. 3, p. 710, Abs. No. 26461w (1980).

*Primary Examiner*—Emily Bernhardt
*Attorney, Agent, or Firm*—Steve T. Zelson; Elias J. Lambiris

[57] ABSTRACT

Piperazinyl derivatives of the general formula I

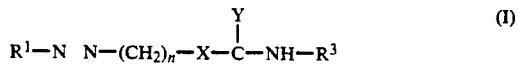

wherein
R$^1$ represents substituted phenyl, 1- or 2-diazanaphthyl, azadiazanaphtyl or diazanaphtyl groups; n is 1, 2, 3 or 4; X is —O— or

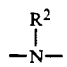

wherein R$^2$ is hydrogen, C$_{1-6}$-alkyl or C$_{3-8}$-cycloalkyl; Y is =O or =S or =NZ wherein Z is hydrogen, C$_{1-6}$-alkyl or —CN and R$^3$ is selected from a group consisting of various structures have been found to exhibit high affinity for various receptor subtypes including the 5-HT$_2$ receptor, the 5-HT$_{1A}$ receptor, the alpha$_1$ receptor the dopamine receptor or a combination of these and may therefore be useful for treating CNS system, cardiovascular system and gastrointestinal disorders.

27 Claims, No Drawings

PIPERAZINYL DERIVATIVES AND METHODS OF TREATING CENTRAL NERVOUS SYSTEM AILMENTS RELATING TO THE 5-HT$_2$ RECEPTOR SYSTEM

It has long been known that serotonin (5-hydroxytryptamine, hereinafter referred to as 5-HT) is a neurotransmitter in the central nervous system (CNS). In particular, over the last decade intensive pharmacological research directed to serotonergic neurotransmitter functions has taken place. It is now generally accepted that in the CNS there are at least five different subtypes of 5-HT binding sites or receptors, which types are identifiable as 5-HT$_{1A}$, 5-HT$_{1B}$, 5-HT$_{1C}$, 5-HT$_2$ and 5-HT$_3$, respectively. Differentiation of the 5-HT receptor subtypes is mainly based on their binding characteristics as characterized by specific radio ligands. For example, the ligand 8-hydroxy-2-(di-n-propylamino)tetralin (8-OH-DPAT) binds with high affinity to 5-HT$_{1A}$ receptors, while another ligand, a 2,4(1H,3H)- quinazolinedione derivative (adopted name: ketanserin) exhibits high affinity for the 5-HT$_2$ receptor subtype. It is worth noting that none of these synthetic ligands have any chemical resemblance whatsoever to the physiological binding partner, i.e. 5-HT. For a recent review of 5-HT receptor ligand interactions reference is made to R.A. Glennon, Neuroscience and Biobehavioral Reviews, 14 (1990), 35-47.

The recent introduction of buspirone having a selectivity for 5-HT$_{1A}$ receptors, as an effective anxiolytic agent (U.S. Pat. No. 3,717,634) into the United States marketplace has stimulated interest in development of second-generation anxiolytic agents.

E.P. Publ. No. 343-961-A2 discloses the treatment of anxiety and depression with aryl and heteroaryl piperazinyl carboxamides, which demonstrated selectivity of the 5-HT$_{1A}$ and 5-HT$_2$. 5-HT$_2$ antagonists, such as Ritanserin, lack 5-HT$_{1A}$ affinity but demonstrate clinical efficacy as anxiolytic-antidepressant agents (Barone et al., Drug Clin. Pharm., 20, 770, 1986).

Compounds reducing 5-HT neurotransmission has been suggested to be useful for the treatment of ischemic brain damage, e.g. 5-HT$_{1A}$ agonists, such as 8-hydroxy-DPAT (EP-360-077A, EP-345-948-A2), and 5-HT$_2$ antagonists, such as naftidrofuryl (Brain Res. 1989, 494 (2) 397-90), are described to exhibit a protective effect on ischemic neuronal damage in the gerbil. Risperidone which is a potent antagonist both serotonin 5-HT$_2$ and dopamine D$_2$ receptors is described to have antipsychotic properties, and serotonergic mechanisms is described to be involved as active factors, or inducing processes, in the organization of sleep (Neuropharmacology, 19, (1980), 163).

One of the atypical neuroleptics is clozapine, which has an unprecedented antipsychotic potential, especially in otherwise treatment-refractory patients. Clozapine nonselectively binds to both 5HT$_2$, alpha$_1$-adrenergic and dopaminergic receptors.

Related piperazine derivatives described in U.S. Pat. No. 4,882,432, U.S. Pat. No. 4,202,898, GB patent 952,142, EP-A1-402,644, EP-B1-15,615 and U.S. Pat. No. 2,836,595 are claimed to have biological activity.

This invention relates to novel piperazinyl derivatives, methods for making them and pharmaceutical compositions containing them.

The compounds of this invention, demonstrate high affinity for various receptor subtypes including the 5-HT$_2$ receptor, the 5HT$_{1A}$ receptor, the 5-HT$_{1B}$ receptor, the alpha$_1$ these. This invention relates to the use of said compounds as medicaments useful for treating CNS- system, cardiovascular system and gastrointestinal disorders, such as treatment of anxiety, sleep disorders, depression, psychoses, schizophrenia, migraine, ischemic neuronal damage, astma, hypertension, urticaria, analgesia and emesis.

More particularly the present invention relates to compounds of formula I $$R^1-N\underset{\diagdown\_\diagup}{\overset{\diagup\overline{\phantom{xx}}\diagdown}{}}N-(CH_2)_n-X-\overset{\overset{Y}{\|}}{C}-NH-R^3 \quad (I)$$

wherein
R$^1$ represents
a phenyl group, substituted with C$_{1-6}$-alkoxy, halogen, cyano, nitro or perhalomethyl, or
a 1- or 2-naphthyl group, which may be substituted with C$_{1-6}$-alkyl, C$_{3-8}$-cycloalkyl, C$_{1-6}$-alkoxy, halogen, cyano, nitro or perhalomethyl, or
either a azanaphthyl or a diazanaphthyl group, either of which may be substituted with C$_{1-6}$-alkyl, C$_{3-8}$-cycloalkyl, C$_{1-6}$-alkoxy, halogen, cyano, nitro or perhalomethyl;
n is 1, 2, 3 or 4;
X is —O— or $$-\underset{\underset{R^2}{|}}{N}-$$

wherein
R$^2$ is hydrogen, C$_{1-6}$-alkyl or C$_{3-8}$-cycloalkyl;
Y is =O, =S, or =NZ
wherein Z is hydrogen, C$_{1-6}$-alkyl or CN;
R$^3$ is selected from the group consisting of:

[benzothiazole structure] or [substituted phenyl with R$^4$, R$^5$, R$^6$, R$^7$]

wherein
R$^4$, R$^5$, R$^6$ and R$^7$ which may be identical or different represent hydrogen, alkyl, halogen, C$_{1-6}$-alkoxy, perhalomethyl;
or R$^6$ and R$^7$ are hydrogen atoms and R$^5$ when taken together with R$^4$ forms

[dioxole-type ring structure $-O-(CH)_n-O-$]

wherein n=1, 2 or 3;
or R$^4$ and R$^5$ are hydrogen atoms and R$^6$ and R$^7$ when taken together are —(CH$_2$)$_n$— wherein n=3, 4 or 5, provided that R$^4$, R$^5$, R$^6$ and R$^7$ are not hydrogen at the same time.

The compounds of formula I may be converted into any physiologically acceptable salt thereof.

The invention includes within its scope all optical isomers of compounds of the general formula I and their mixtures including racemic mixtures thereof.

Compounds of the general formula I were tested for binding to various CNS receptor subtypes:

Detailed conditions for the receptor binding assay in vitro are tabulated below.

In-Vitro Inhibition of Dopamine D2 Receptor Binding,

Method Description

Principle

Radioactive-labelled ligand $^3$H-Spiroperidol is incubated with isolated cell-membrane fragments at 37° C. for a given period of time. Following completed incubation, the incubate is filtered through GF/B filters which are rinsed following filtration to remove unspecifically adhered radioactivity. As opposed to low- molecular compounds, membrane fragments are not rinsed through the filters, the radioactivity bound to the filters is indicative of the amount of ligand bound specifically as well as nonspecifically to the membranes.

Tissue Preparation

The procedure is performed in ice bath. Polytron kinematica is rinsed with milli-Q-H$_2$O before and after use. Male Wistar rats, 150–200 g are decapitated, striatum is removed quickly and weighed (approx. 50 mg). Striatum is transferred to a centrifuging vial containing 10 ml ice-cold D2 buffer. Homogenization is performed applying polytron kinematica (homogenizer) setting 6 for 20 sec. The homogenizer is rinsed with 10 ml D2 buffer in another centrifuging vial. The 10 ml rinsing buffer is added to the tissue vial. Centrifugation at 18,000 rpm for 10 min. at 4° C. Final pellet is transferred to 1,000×vol. of same buffer. (Ex. 50 mg striatum in 50 ml D2 buffer). Can be stored at 0° C. for at least 4 hours. Note that the tissue must homogeneous (uniform) before use. If not, brief homogenization is performed.

Assay 2,500 μl tissue (homogeneous)
25 μl $^3$H-Spiroperidol (0.05 nM)
25 μl test substance/H$_2$O/blind (Domperidone 0.2 μM)

Incubation for 20 min. at 37° C.–10 min. on ice bath.

10 ml ice-cold 0.9% NaCl is added to the tubes and filtered through GF/B filters (use gloves). This procedure is repeated. The filters are placed in counting vials and 4 ml opti-flour is added (perform in fume cupboard, use gloves). Counting is performed at window 0–19 of the beta-counter (Pachard). Note that receptor box and lid are rinsed thoroughly in H$_2$O after use to avoid contamination. Further, the analytical site is cleaned carefully every day after use.

Test Substances

Dissolved in H$_2$O, EtOH, MeOH or DMSO and further diluted in H$_2$O. The D2 binding will stand concentrations of up to approx. 20% of these solvents without affecting the binding. Most stock solutions are stable at 4° C., attention is, however, paid to any precipitation, change in colour etc. Test-substance dilutions are always made fresh every day. When weighing out test substances, it is attempted to weigh out approx. 1 mg of substance. Less than 0.8 mg must never be weighed out and only infrequently more than 2 mg (for economy reasons), dependent, however, on conc./assay.

Results

The test value is given as IC$_{50}$ indicating the concentration inhibiting specific binding by 50%.

$$\frac{\text{Conc.}}{\frac{100}{\text{"\% control"}} - 1} = IC_{50} \text{ (nM)}$$

In-Vitro Inhibition of Alpha$_1$-Receptor Binding,

Method Description

Principle

Radioactive-labelled ligand $^3$H-Prazosin is incubated with isolated cell-membrane fragments at 25° C. for a given period of time. Following completed incubation, the incubate is filtered through GF/B filters, which are rinsed following filtration to remove unspecifically adhered radioactivity. As opposed to low- molecular compounds, membrane fragments are not rinsed through the filters, the radioactivity bound to the filters indicates the amount of ligand bound specifically as well as nonspecifically to the membranes.

Tissue Preparation

The procedure is performed in ice bath. Polytron kinematica is rinsed with milli-Q-H$_2$O before and after use. Male Wistar rats, 150–200 g are decapitated, cortex is removed quickly and weighed (approx. 500 mg). Cortex is transferred to a centrifuging vial containing 10 ml ice-cold D2 buffer. Homogenization applying polytron kinematica (homogenizer) setting 6 for 20 sec. The homogenizer is rinsed with 10 ml D2 buffer in another centrifuging vial. The 10 ml rinsing buffer is added to the tissue vial. Centrifugation at 18,000 rpm for 12 min. at 4° C. This is repeated once. Final pellet is added to 400×vol. of same buffer. (Ex. 500 mg cortex in 200 ml D2 buffer). Can be stored for 30 min. at 0° C.

Assay 2,000 μl tissue
25 μl $^3$H-Prazosin (0.5 nM)
25 μl test substance/H$_2$O/blind Phentolamine (10 μM)

Incubation for 30 min. at 25° C.

10 ml of ice-cold 0.9% NaCl is added to the tubes and filtered through GF/B filters (use gloves). This procedure is repeated. Filters are placed in counting vials and 4 ml opti-flour is added (perform in fume cupboard, use gloves). Counting is performed at window 0–19 of the betacounter (Pachard). Note that receptor box and cover are rinsed thoroughly in H$_2$O after use to avoid contamination. Further, the analytical site is cleaned carefully every day after use.

Test Substances

Dissolved in H$_2$O, EtOH, MeOH or DMSO and further diluted in H$_2$O. The binding will stand concentrations of up to approx. 5% of these solvents without affecting the binding. Most stock solutions are stable at 4° C. Attention should, however, be paid to any precipitation, change in colour etc. Test-substance dilutions are always prepared fresh every day. When weighing out test substances, it is attempted to weigh out approx. 1 mg of substance. Less than 0.8 mg must never be weighed out and only infrequently more than 2 mg (for economy reasons) dependent, however, on conc./ass.

Results

The test value is given as $IC_{50}$ indicating the concentration inhibiting specific binding by 50%.

$$\frac{\text{Conc.}}{\frac{100}{\text{"\% control"}} - 1} = IC_{50} \text{ (nM)}$$

In-Vitro inhibition of $5HT_{1A}$ receptor binding

Method Description

Principle

Radioactive-labelled ligand $^3$H-80H-DPAT is incubated with isolated cell-membrane fragments at 37° C. for a given period of time. Following completed incubation, the incubate is filtered through GF/F filters which are rinsed after filtration to remove unspecifically adhered radioactivity. As opposed to low-molecular compounds, membrane fragments are not rinsed through the filters, the radioactivity bound to the filters indicates the amount of ligand bound specifically as well as non-specifically to the membranes.

Tissue Preparation

Male Wistar rats, 150-200 g are decapitated, and frontal cortex (approx. 200 mg) and hippocampus (approx. 70 mg) homogenized in 2×10 ml ice-cold DPAT buffer for 20 sec. applying polytron kinematica setting 6. Centrifuged at 20,000 rpm for 10 min. at 4° C. The pellet is transferred to 2×10 ml ice-cold DPAT buffer, homogenized for 20 sec. and preincubated for 10 min. at 37° C. Centrifuged at 20,000 rpm for 10 min. at 4° C. Final pellet added to 125×vol. of same buffer with 10 μM paragylin added (ex. 270 mg tissue in 33.75 ml DPAT buffer containing paragylin). Prepared fresh every day. Use within 30 minutes.

Assay 1,250 μl tissue 25 μl $^3$H-80H-DPAT (1 nM) 25 μl test substance/H$_2$O/blind serotonin (10 μM)

Incubation at 37° C. for 10 min.—at 10 sec. intervals. To the tubes is added 10 ml ice-cold 0.9% NaCl. Filtration through GF/F filters (use gloves). This procedure is repeated. Filters are placed in counting vials and 4 ml optiflow added (prepare in fume cupboard, use gloves). Counted at window 0-19 of the beta- counter (Pachard). Note that receptor box and lid are rinsed thoroughly in H$_2$O after use to avoid contamination. Further the analytical site is cleaned carefully every day.

Test substances

Dissolved in H$_2$O, EtOH, MeOH or DMSO and further diluted in H$_2$O. The DPAT binding will stand concentrations of up to approx. 5% of these solvents without affecting the binding. Most stock solutions are stable at 4° C. Attention should, however, be paid to any precipitation, change in colour etc. Test-substance dilutions are always prepared fresh every day. When weighing out test substances, it is attempted to weigh out approx. 1 mg of substance. Less than 0.8 mg must never be weighed out and only infrequently more than 2 mg (for economy reasons) dependent, however on conc./assay.

Results

The test value is given as $IC_{50}$, i.e. the concentration inhibiting specific binding by 50%.

$$\frac{\text{Conc.}}{\frac{100}{\text{"\% control"}} - 1} = IC_{50} \text{ (nM)}$$

In Vitro Inhibition of $5HT_2$-Receptor Binding

Method Description

Principle

Radioactive-labelled ligand $^3$H-Ketanserine is incubated with isolated cell-membrane fragments at 37° C. for a given period of time. Following completed incubation, the incubate is filtered through GF/B filters which are rinsed after filtration to remove unspecifically adhered radioactivity. As opposed to low-molecular compounds, membrane fragments are not rinsed through the filters, the radioactivity bound to the filters indicates the amount of ligand bound specifically as well as non-specifically to the membranes.

Tissue Preparation

The preparation is made in ice bath. Polytron kinematica is rinsed with milli-Q-H$_2$O before and after use. Male Wistar rats, 150-200 g are decapitated. Frontal cortex is removed quickly and weighed (approx. 200 mg). Frontal cortex is added to centrifuging vial containing 10 ml ice-cold D2 buffer. Homogenization applying polytron kinematica (homogenizer) setting 6 for 20 sec. The homogenizer is rinsed with 10 ml D2 buffer in another centrifuging vial. The 10 ml rinsing buffer is added to the tissue vial. Centrifuged at 18,000 rpm for 10 min. at 4° C. Final pellet is transferred to 125×vol. of same buffer. (Ex. 200 mg in 25 ml D2 buffer). Can be stored for approx. 30 min. at 0° C.

Assay

1250 μl tissue
25 μl $^3$H-Ketanserine (0.4 nM)
25 μl test substance/H$_2$O/blind cyproheptadine (2 μM)

Incubation for 15 min. at 37° C.

10 ml ice-cold 0.9% NaCl is added to the tubes. Filtration is performed through GF/B filters (use gloves). This procedure is repeated. Filters are placed in counting vials, and 4 ml opti- flour is added (prepare in fume cupboard, use gloves). Counting at window 0-19 of the beta-counter (Pachard). Note that receptor box and lid are rinsed thoroughly in H$_2$O after use to avoid contamination. Further the analytical site is cleaned carefully every day.

Test Substances

Dissolved in H$_2$O, EtOH, MeOH or DMSO and further diluted in H$_2$O. The $5HT_2$ binding will stand concentrations of up to approx. 5% of these solvents without affecting the binding. Most stock solutions are stable at 4° C. Attention should, however, be paid to any precipitation, change in colour etc. Test-substance dilutions are always made fresh every day. When weighing out test substance, it is attempted to weigh out approx. 1 mg of substance. Less than 0.8 mg must never be weighed out and only infrequently more than 2 mg (for economy reasons) dependent, however, on conc./assay.

Results

The test value is given as $IC_{50}$, i.e. the concentration inhibiting specific binding by 50%.

$$\frac{\text{Conc.}}{\frac{100}{\text{"\% control"}} - 1} = IC_{50} \text{ (nM)}$$

Antagonism of Acetic Acid-Induced Writhings In Mice

Principle

In mice i.p. injection of acetic acid induces a writhing syndrome which is antagonized by analgesics (Siegmund et al., 1957; Eckhardt et al., 1957).

Method

Acetic acid 0.5 per cent is injected i.p. (0.15 ml/10 g body weight) to 6 mice (NMRI, either sex weighing 20-25 g) pretreated with physiological saline (controls) and to 6 mice pretreated with test substance. In the controls acetic acid induces a syndrome characterized by contraction of abdomen, turning of trunk and extension of hind limbs. Saline and test substances are administered s.c. 30 min. before acetic acid. The number of writhings is counted 5-15 min. after injection of acetic acid.

Results

Initially, the dose of test substance is equivalent to 5-10 per cent of $LD_{50}$ If this dose decreases writhings, 3-5 dose levels are tested. The activity is expressed as per cent protection:

$$100 - \left(\frac{\text{average writhings of treated group}}{\text{average writhings of daily control groups}}\right) \times 100$$

The effect of active substances is evaluated by a dose response curve, log dose on the abscissa, and per cent protection on the ordinate. The potency is expressed as the dose ($ED_{50}$ in mg/kg giving 50 per cent protection against writhings.

Specificity of Test

Analgesics and various other drugs inhibit acetic acidinduced writhings in mice. This test is used as a screening test for analgesics. Additional results from other screening tests are required to exclude active anti-writing substances without analgesic effect.

References

Eckhardt, E. et al. Etiology of chemically induced writhing in mouse and rat. Proc. Soc. exp. Biol. 98, 186-188, 1958.

Siegmund, e. et al. A method for evaluating both non-naracotic and narcotic analgesics. Proc. Soc. exp. Biol. 95, 729-731, 1957.

The following results are representative of the ones obtained:

TABLE 1

| Test | Receptor binding $IC_{50}$ (nM) | | | |
|---|---|---|---|---|
| | $5HT_{1A}$ | $5HT_2$ | $D_2$ | $\alpha_1$ |
| Example 3 | >300 | 7.5 | 120 | 45 |

TABLE 1-continued

| Test | Receptor binding $IC_{50}$ (nM) | | | |
|---|---|---|---|---|
| | $5HT_{1A}$ | $5HT_2$ | $D_2$ | $\alpha_1$ |
| Example 8 | >1000 | 10 | 720 | 61 |
| Example 19 | >1000 | 22 | 150 | 122 |
| Example 24 | 61 | 49 | n.t. | 7.5 |
| Example 34 | 1.6 | 13 | 4.3 | 144 |

TABLE 2

| Antagonism of acetic acid-induced writhings in mice | |
|---|---|
| Compound | $ED_{50}$ (mg/kg) |
| Pethidine | 9.3 |
| Morphine | 0.26 |
| Example 3 | 12.0 |
| Example 15 | 5.6 |
| Example 18 | 7.0 |

The compounds of the invention and physiologically acceptable salts thereof may be prepared by a variety of synthetic routes, which includes reacting a compound of formula II $$Y=C=N-R^3 \quad \text{(II)}$$

where Y and $R^3$ have the meaning set forth above, with the compounds of formula III

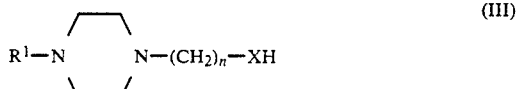

(III)

wherein $R^1$, n and X have the meaning set forth above to form a compound of formula I.

For instance an isocyanate or isothiocyanate of 3,4,5-trimethoxyaniline, prepared by refluxing 3,4,5-trimethoxyaniline and phosgene or thiophosgene respectively in toluene, may be reacted with the desired piperazinyl alkylamine or alkylhydroxy intermediate to obtain the desired urea or carbamate of formula I.

Compounds of formula I, wherein X is

and Y is =NZ, and $R^2$ and Z have the meanings set forth above are prepared by standard procedures as described in e.g., H.J. Petersen et al, J. Med. Chem. (1978) 21, 773-781.

The procedure includes reacting a compound of formula IV

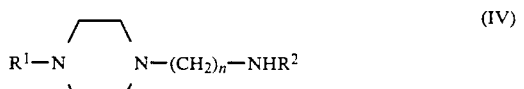

(IV)

wherein $R^1$, n and $R^2$ have the meanings set forth above, with a compound of formula V

(V)

wherein R³ and Z have the meanings set forth above, or reacting a compound of formula VI

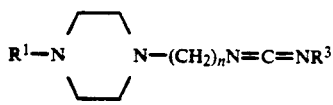 (VI)

prepared from a compound of formula VII

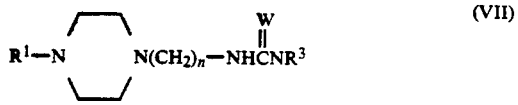 (VII)

wherein R¹ and R³ have the meanings set forth above and W is O or S, with NH₂—Z, wherein Z has the meaning set forth above.

The purified reaction product may be converted into a physiologically acceptable salt. Such salts include acid addition salts formed with inorganic or organic acids, for example hydrochlorides, hydrobromides, sulphates, nitrates, oxalates, phosphates, tartrates, citrates, fumarates, maleates, succinates, and sulphonates e.g. mesylates.

If desirable, selected salts may be subjected to further purification by recrystallization.

The compounds of the invention, together with a conventional adjuvant, carrier, or diluent, and if desired a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compound of the invention is dispensed in unit dosage form comprising 0.05–100 mg in a pharmaceutically-acceptable carrier per unit dosage.

A typical tablet which may be prepared by conventional tabletting techniques contains:

| | |
|---|---|
| Active compound | 1.0 mg |
| Lactosum | 67.9 mg ph. Eur. |
| Avicel ® | 31.4 mg |
| Amberlite ® IRP 88 | 1.0 mg |
| Magnesii stearas | 0.25 mg Ph. Eur. |

The following examples illustrate the specific methods employed in production of a representative number of compounds embraced by this invention.

EXAMPLE 1

4-(4-Chlorophenyl)-1-[3-(3,4,5-trimethoxyphenylcarbamoyloxy)propyl]piperazine, hydroohloride A mixture of 3,4,5-trimethoxyaniline (365 mg; 2.0 mmol) in toluene (20 ml) and phosgene (6 ml 20% in toluene; 12 mmol) was refluxed for 6 h. The solvent was removed under reduced pressure to give crude 3,4,5-trimethoxyphenylisocyanate. The crude product was added 3-[4-(4-chloro-phenyl)-1-piperazinyl]propanol (800 mg; 3.1 mmol) in toluene (25 ml) and refluxed for 16 h. The solvent was evaporated and the residue taken up in ethanol, which was treated with hydrogen chloride in ether. Recrystallization from ethanol/ether afforded 620 mg of the title compound M.p. 173.5°–174.5° C.

EXAMPLE 2

4-(2-Methoxyphenyl)-1-[3-(3,4,5-trimethoxyphenylcarbamoyloxy)propyl]piperazine, hydrochloride A mixture of 3,4,5-trimethoxyphenylisocyanate (420 mg; 2.0 mmol) (produced as in Example 1) and 3-[4-(2-methoxy-phenyl) -1-piperazinyl]propanol (500 mg; 2 mmol) in toluene (25 ml) was refluxed for 16 h. The reaction mixture was then concentrated and the residue taken up in ethanol which was treated with hydrogen chloride in ether. Recrystallization from methanol/ether afforded 710 mg of the title compound. M.p. 201°–204° C. MS (70 eV): m/z 459 (44%, M+), 250 (54), 209 (61), 205 (100), 194 (63), 136 (59), 70 (77).

EXAMPLE 3

4-(2-Chlorophenyl)-1-[3-(3,4,5-trimethoxyphenylcarbamoyloxy)propyl]piperazine, hydrochloride A mixture of 3,4,5-trimethoxyphenylisocyanate (420 mg; 2.0 mmol) (produced as in Example 1) and 3-[4-(2-chloro-phenyl) -1-piperazinyl]propanol (500 mg; 20 mmol) in toluene (25 ml) was refluxed for 16 h. The solvent was evaporated and the residue taken up in ethanol, which was treated with hydrogen chloride in ether. Recrystallization from ethanol/ether afforded 400 mg of the title compound. M.p. 185°–187° C. MS (70 eV): m/z 463 (6%, M+), 254 (30), 209 (100), 194 (52), 166 (34), 70 (58).

EXAMPLE 4

4-(3-Chlorophenyl)-1-[3-(3,4,5-trimethoxyphenylcarmaboyloxy)propyl]piperazine, hydrochloride A mixture of 3,4,5-trimethoxyphenylisocyanate (420 mg; 2.0 mmol) (produced as in Example 1) and 3-[4-(3-chloro-phenyl) -1-piperazinyl]propanol (500 mg; 2.0 mmol) in toluene (25 ml) was refluxed for 16 h. The solvent was evaporated and the residue taken up in ethanol, which was treated with hydrogen chloride in ether. Recrystallization from ethanol/ether afforded 500 mg of the title compound. M.p. 203.5°–205° C. MS (70 eV): m/z 463 (7%, M+), 254 (21), 209 (100), 194 (42), 166 (24), 70 (42).

EXAMPLE 5

4-(3-Trifluoromethylphenyl)-1-[3-(3,4,5-trimethoxyphenylcarbamoyloxy)propyl]piperazine, hydrochloride A mixture of 3,4,5-trimethoxyphenylisocyanate (420 mg; 2.0 mmol) (produced as in Example 1) and 3-[4-(3-trifluoromethylphenyl) -1-piperazinyl]propanol (575 mg; 2.0 mmol) in toluene (20 ml) was refluxed for 16 h. The reaction mixture was then concentrated and submitted to flash chromatography on silica gel 60 eluting with toluene graduated to toluene/ethyl acetate (1:5). The product was taken up in ethyl acetate, which was treated with hydrogen chloride in ether. Recrystallization from methanol/ether afforded 450 mg of the title compound. M.p. 203°–305° C. MS (70 eV): m/z 497 (16%, M+), 288 (46), 243 (100), 209 (79), 194 (39), 172 (23), 70 (49).

EXAMPLE 6

4-(3-Trifluoromethylphenyl)-1-[2-(3,4,5-trimethoxyphenylcarbamoyloxy)ethyl]piperazine, hydrochloride A mixture of 3,4,5-trimethoxyphenylisocyanate (420 mg; 2.0 mmol) (produced as in Example I) and 2-[4-(3-trifluoromethylphenyl) -1-piperazinyl]ethanol (550 mg; 2.0 mmol) in toluene (20 ml) was refluxed for 16 h. The reaction mixture was then concentrated and submitted to flash chromatography on silica gel 60 eluting with toluene graduated to toluene/ethyl acetate (1:1). The product was taken up in ethanol which was treated with hydrogen chloride in ether. Recrystallization from methanol/ether afforded 600 mg of the title compound. M.p. 191°–192° C. MS (70 eV): m/z 483 (32%, M+), 257 (38), 243 (100), 227 (49), 209 (36), 200 (70), 194 (41), 182 (27), 172 (46), 145 (32), 70 (63).

EXAMPLE 7

4-(4-Methoxyphenyl)-1-[3-(3,4,5-trimethoxyphenylcarbamoyloxy)propyl]piperazine, hydrochloride A mixture of 3,4,5-trimethoxyphenylisocyanate (420 mg; 2.0 mmol) (produced as in Example 1) and 3-[4-(4-methoxy-phenyl) -1-piperazinyl]propanol (500 mg; 2.0 mmol) in toluene (20 ml) was refluxed for 16 h. The reaction mixture was then concentrated and submitted to flash chromatography on silica gel 60 eluting with toluene graduated to toluene/ethyl acetate (1:1). The product was taken up in ethanol which was treated with hydrogen chloride in ether. Recrystallization from methanol/ether afforded 540 mg of the title compound. M.p. 210°–214° C. MS (70 eV): m/z 459 (77%, M+), 250 (84), 209 (72), 205 (100), 194 (82), 166 (42), 135 (59), 120 (61), 70 (94).

EXAMPLE 8

4-(4-Fluorophenyl)-1-[3-(3,4,5-trimethoxyphenylcarbamoyloxy)propyl]piperazine, hydrochloride A mixture of 3,4,5-trimethoxyphenylisocyanate (420 mg; 2.0 mmol) (produced as in Example 1) and 3-[4-(4-fluoro-phenyl) -1-piperazinyl]propanol (475 mg; 2.0 mmol) in toluene (20 ml) was refluxed for 16 h. The reaction mixture was then concentrated and submitted to flash chromatography on silica gel 60 eluting with toluene graduated to toluene/ethyl acetate (1:1). The product was taken up in ethanol which was treated with hydrogen chloride in ether. Recrystallization from methanol/ether afforded 420 mg of the title compound. M.p. 207°–208° C. MS (70 eV): m/z 447 (13%, M+), 238 (42), 209 (55), 194 (56), 193 (100), 123 (59), 95 (35), 70 (82).

EXAMPLE 9

4-(1-Naphthyl)-1-[3-(3,4,5-trimethoxyphenylcarbamoyloxy)propyl]piperazine, hydrochloride A mixture of 3,4,5-trimethoxyphenylisocyanate (420 mg; 2.0 mmol) (produced as in Example 1) and 3-[4-(1-naphthyl)1-piperazinyl]propanol (540 mg; 2.0 mmol) in toluene (20 ml) was refluxed for 16 h. The reaction mixture was then concentrated and submitted to flash chromatography on silica gel 60 eluting with toluene graduated to toluene/ethyl acetate (1:1). The product was taken up in ethanol which was treated with hydrogen chloride in ether. Recrystallization from methanol/ether afforded 610 mg of the title compound. M.p. 249°–250° C. MS (70 eV): m/z 479 (12%, M+), 270 (100), 225 (90), 209 (87), 194 (90), 166 (49), 154 (61), 127 (41), 70 (58).

EXAMPLE 10

4-(4-Methoxyphenyl)-1-[2-(3,4,5-trimethoxyphenylcarbamoyloxy)ethyl]piperazine, hydrochloride A mixture of 3,4,5-trimethoxyphenylisocyanate (420 mg; 2.0 mmol) (produced as in Example 1) and 2-[4-(4-methoxy-phenyl) -1-piperazinyl]ethanol (270 mg; 2.0 mmol) in toluene (30 ml) was refluxed for 16 h. The reaction mixture was then concentrated and submitted to flash chromatography on silica gel 60 eluting with toluene graduated to toluene/ethyl acetate (1:4). The product was taken up in ethanol which was treated with hydrogen chloride in ether. Recrystallization from methanol/ether afforded 750 mg of the title compound. M.p. 193°–196° C. MS (70 eV): m/z 445 (90%, M+), 236 (49), 218 (46), 209 (55), 205 (100), 194 (68), 162 (62), 135 (42), 120 (48), 70 (83).

EXAMPLE 11

N-3-[4-(2-Chlorophenyl)piperazin-1-yl]propyl-N'-(3,4ethylenedioxyphenyl)thiourea, HCl To a mixture of 1,4-benzodioxan-6-amine (15.1 g; 100 mmol) and triethylamine (20.2 g, 200 ml) in toluene (350 ml) was added dropwise over 10 min. thiophosgene (11.5 g, 100 mmol) in toluene (50 ml). The mixture was stirred at 80° C. for 30 min., cooled to room temperature and filtered. The filtrate was evaporated. The product was redissolved in toluene and concentrated in vacuo. The resulting oil was taken up in warm petroleum ether, which was filtered. The filtrate was concentrated to a small volume, which afforded 7.2 g of 3,4-ethylenedioxyphenylisothiocyanate. 3,4-Ethylenedioxyphenylisothiocyanate (1.1 g; 5.7 mmol) in toluene (15 ml) was added to 3-[4-(2-chlorophenyl)piperazin-1-yl]propylamine (1.45 g, 5.7 mmol) in toluene (45 ml). The mixture was refluxed for 6 h, cooled to room temperature and purified by column chromatography on silica gel 60 eluting with toluene graduated to toluene/ethyl acetate (1:1). The product was triturated with petroleum ether and redissolved in ethanol. Addition of hydrogen chloride in ether precipitated the title compound, which was recrystallized from ethanol to give 180 mg. M.p. 210°–212° C. MS (70 eV): m/z 447 (M+, 1%), 445 (1), 295 (4), 193 (100), 166 (10), 151 (20).

EXAMPLE 12

N-3-[4-(2-Chlorophenyl)piperazin-1-yl]propyl-N'-cyano-N''-(3, 4-ethylenedioxyphenyl)guanidine, oxalate A mixture of S-methyl-N-3,4-ethylenedioxyphenyl-N'-cyanothiourea (0.5 g; 2 mmol) (produced by a method described in J. Med. Chem. (1978) 21, 773–781 and in J. Chem. Soc. (1948) p. 1630, from 3,4-ethylenedioxyphenylisothiocyanate of Example 11, cyanamide and methyliodide) and 3-[4(2-chlorophenyl)-piperazin-1-yl]propylamine (0.5 g; 2 mmol) in pyridine was stirred at room temperature for 5 days and at 60° C. for 24 h. The reaction mixture was concentrated in vacuo and triturated in ethyl acetate. The product dissolved in acetone (50 ml) and oxalic acid (230 mg in acetone (2 ml)) was added to precipitate the desired product as 270 mg white crystals, M.p. 137°–139° C. MS (70 eV): m/z 454 (M+, 4%), 453 (M+·1, 8), 314 (10), 301 (20), 288 (100), 259 (40), 245 (29).

EXAMPLE 13

4-(2-Chlorophenyl)-1-[3-(3,4-methylenedioxyphenyl-carbamoyloxy)propyl]piperazine, hydrochloride A mixture of 3,4-methylenedioxyaniline (275 mg; 2.0 mmol) in toluene (15 ml) and phosgene (4.75 ml; 20% in toluene; 9 mmol) was refluxed for 6 h. The solvent was removed under reduced pressure to give crude 3,4-methylenedioxyphenylisocyanate. The crude product was added to 3-[4-(2-chlorophenyl)-1-piperazinyl]-propanol (510 mg; 2.0 mmol) in toluene (30 ml) was refluxed for 16 h. The reaction mixture was then concentrated and submitted to flash chromatography on silica gel 60 eluting with toluene graduated to toluene/ethyl acetate (1:3). The product was taken up in ethanol which was treated with hydrogen chloride in ether. Recrystallization from methanol/ether afforded 550 mg of the title compound. M.p. 211°–213° C. MS (70 eV): m/z 37%, M+), 254 (28), 209 (100), 163 (75), 138 (32), 70 (42).

EXAMPLE 14

4-(1-Naphthyl)-1-[3-(3,4-methylenedioxyphenylcarbamoyloxy)propyl]piperazine, hydrochloride A mixture of 3,4-methylenedioxyphenylisocyanate (330 mg; 2.0 mmol) (produced as in Example 13) and 3-[4-(1-naphthyl)-1-piperazinyl]propanol (540 mg; 2.0 mmol) in toluene (30 ml) was refluxed for 16 h. The reaction mixture was then concentrated and submitted to flash chromatography on silica gel 60 eluting with toluene graduated to toluene/ethyl acetate (1:3). The product was taken up in ethanol which was treated with hydrogen chloride in ether. Recrystallization from methanol/ether afforded 820 mg of the title compound. M.p. 234°–236° C. MS (70 eV): m/z 433 (23%, M+), 270 (61), 225 (72), 163 (62), 154 (52), 141 (18), 127 (32), 42 (100).

EXAMPLE 15

4-(3-Chlorophenyl)-1-[3-(3,4-methylenedioxyphenyl-carbamoyloxy)propyl]piperazine, hydrochloride A mixture of 3,4-methylenedioxyphenylisocyanate (330 mg; 2.0 mmol) (produced as in Example 13) and 3-[4-(3-chlorophenyl)-1-piperazinyl]propanol (510 mg; 2.0 mmol) in toluene (30 ml) was refluxed for 16 h. The reaction mixture was then concentrated and submitted to flash chromatography on silica gel 60 eluting with toluene graduated to toluene/ethyl acetate (1:3). The product was taken up in ethanol which was treated with hydrogen chloride in ether. Recrystallization from methanol/ether afforded 850 mg of the title compound M.p. 182°–184° C. MS (70 eV): m/z 417 (42%, M+), 254 (24), 209 (100), 194 (7), 163 (70), 136 (37), 70 (51).

EXAMPLE 16

4-(4-Chlorophenyl)-1-[3-(3,4-ethylenedioxyphenylcarbamoyloxy)propyl]piperazine, hydrochloride A mixture of 1,4-benzodioxan-6-amine (300 mg; 2.0 mmol) in toluene (20 ml) and phosgene (10 ml 20% in toluene; 19 mmol) was refluxed for 6 h. The solvent was removed under reduced pressure to give crude 3,4-ethylenedioxyphenylisocyanate. The crude product was added 3-[4-(4-chlorophenyl)-1-piperazinyl]propanol (500 mg; 2.0 mmol) in toluene (10 ml) and refluxed for 16 h. The reaction mixture was then concentrated and submitted to flash chromatography on silica gel 60 eluting with toluene graduated to toluene-/ethyl acetate (1:1). The product was taken up in ethyl acetate, which was treated with hydrogen chloride in ether. Recrystallization from methanol/ether afforded 440 mg of the title compound. M.p. 243°–244° C. MS (70 eV): m/z 431 (31%, M+), 254 (34), 209 (100), 177 (75), 121 (31), 70 (38).

EXAMPLE 17

4-(2-Chlorophenyl)-1-[3-(3,4-ethylenedioxyphenylcarbamoyloxy)propyl]piperazine, hydrochloride A mixture of 3,4-ethylenedioxyphenylisocyanate (2.0 mmol) (produced as in Example 16) and 3-[4-(2-chlorophenyl)-1piperazinyl]propanol (500 mg; 2.0 mmol) in toluene (10 ml) was refluxed for 16 h. The reaction mixture was then concentrated and submitted to flash chromatography on silica gel 60 eluting with toluene graduated to toluene/ethyl acetate (1:5). The product was taken up in ethyl acetate which was treated with hydrogen chloride in ether. Recrystallization from methanol/ether afforded 330 mg of the title compound. M.p. 205°–206° C. MS (70 eV): m/z 431 (14%, M+), 209 (100), 177 (70), 121 (44), 93 (38), 70 (56).

EXAMPLE 18

4-(3-Chlorophenyl)-1-[3-(3,4-ethylenedioxyphenylcarbamoyloxy)propyl]piperazine, hydrochloride A mixture of 3,4-ethylenedioxyphenylisocyanate (2.0 mmol) (produced as in Example 16) and 3-[4-(3-chlorophenyl)-1piperazinyl]propanol (500 mg; 2.0 mmol) in toluene (10 ml) was refluxed for 16 h. The reaction mixture was then concentrated and submitted to flash chromatography on silica gel 60 eluting with toluene graduated to toluene/ethyl acetate (1:5). The product was taken up in ethyl acetate which was treated with hydrogen chloride in ether. Recrystallization from methanol/ether afforded 600 mg of the title compound M p. 226°–230° C. MS (70 eV): m/z 431 (62%, M+), 254 (37), 209 (100), 177 (75), 121 (30), 93 (23), 70 (25).

EXAMPLE 19

4-(4-Chlorophenyl)-1-[3-(6-benzothiazolylcarbamoyloxy)propyl]piperazine, hydrochloride A mixture of 6-aminobenzothiazole (600 mg; 4 mmol) in toluene (40 ml) and phosgene (20 ml 20% in toluene; 40 mmol) was refluxed for 6 h. The solvent was removed under reduced pressure to give crude 6-benzothiazolylisocyanate. To the crude product was added 3-[4-(4-chlorophenyl)-1-piperazinyl]propanol (500 mg; 2.0 mmol) in toluene (20 ml) and refluxed for 16 h. The precipitate was isolated and recrystallized from methanol/ether to give 440 mg of the title compound. M.p. 210°–213° C. MS (70 eV): m/z 430 (13%, M+), 254 (32), 209 (77), 176 (100), 121 (38), 70 (83).

EXAMPLE 20

4-(4-Chlorophenyl)-1-[3-(3,4,5-trichlorophenylcarbamoyloxy)propyl]piperazine, hydrochloride A mixture of 3,4,5-trichloroaniline (400 mg; 2 mmol) in toluene (15 ml) and phosgene (6 ml 20% in toluene; 12 mmol) was refluxed for 6 h. The solvent was removed under reduced pressure to give crude 3,4,5-trichlorophenylisocyanate. To the crude product was added 3-[4-(4-chlorophenyl) -1-piperazinyl]propanol (510 mg; 2.0 mmol) in toluene (30 ml) and refluxed for 16 h. The solvent was evaporated rated and the residue resuspended in ethyl acetate, filtered and evaporated to dryness. The residue was submitted to flash chromatography on silica gel 60 eluting with toluene/ethyl acetate (1:1) graduated to toluene/ethyl acetate (1:3). The product was taken up in ethanol, which was treated with hydrogen chloride in ether to give 730 mg of the title compound. M.p. 211°–212° C. MS (70 eV): m/z 477 (4%, M+), 254 (56), 221 (59), 209 (100), 158 (35), 138 (25), 111 (20), 70 (45).

EXAMPLE 21

4-(3-Trifluoromethylphenyl)-1-[3-(3,4-ethylenedioxyphenylcarbamoyloxy)propyl]piperazine, hydrochloride A mixture of 3,4-ethylenedioxyphenylisocyanate (2.0 mmol) (produced as in Example 16) and 3-[4-(3-trifluoromethyl-phenyl) -1-piperazinyl]propanol (580 mg; 2.0 mmol) in toluene (30 ml) was refluxed for 16 h. To the crude product was added 3-[4-(4-chlorophenyl)-1-piperazinyl]propanol (510 mg; 2.0 mmol) in toluene (30 ml) and refluxed for 16 h. The solvent was evaporated and the residue resuspended in ethyl acetate, filtered and evaporated to dryness. The residue was submitted to flash chromatography on silica gel 60 eluting with toluene/ethyl acetate (1:1) graduated to toluene/ethyl acetate (1:3). The product was taken up in ethanol, which was treated with hydrogen chloride in ether to give 690 mg of the title compound. M.p. 242°–245° C. MS (70 eV): m/z 465 (34%, M+), 450 (11), 288 (25), 265 (21), 243 (100), 177 (61), 70 (79).

EXAMPLE 22

4-(4-Chlorophenyl)-1-(3-[3,4,5-trimethoxyphenyl(thiocarbamoyl)oxy]propyl)piperazine, hydrochloride A mixture of 3,4,5-trimethoxyaniline (440 mg; 2.4 mmol) in toluene (20 ml), thiophosgene (300 mg; 2.5 mmol) and triethylamine (500 mg; 5 mmol) was refluxed for 6 h. The solvent was removed under reduced pressure to give crude 3,4,5-trimethoxyphenylisothiocyanate. To the crude product was added 3-[4-(4-chlorophenyl)-1-piperazinyl]propanol (510 mg; 2.0 mmol) in toluene (40 ml) and refluxed for 16 h. The solvent was evaporated and the residue resuspended in ethyl acetate filtered and evaporated to dryness. The residue was submitted to flash chromatography on silica gel 60 eluting with toluene/ethyl acetate (1:1). The product was taken up in ethanol, which was treated with hydrogen chloride in ether to give 200 mg of the title compound. M.p. 172°–173° C. MS (70 eV): m/z 479 (M+, 0.1%), 254 (55), 225 (100), 209 (80), 182 (32).

EXAMPLE 23

4-(3-Chlorophenyl)-1-(3-[3,4,5-trimethoxyphenyl(thiocarbamoyl)oxy]propyl)piperazine, hydrochloride A mixture of 3,4,5-trimethoxyphenylisothiocyanate (2.0 mmol) (produced as in Example 22) and 3-[4-(3-chlorophenyl) -1-piperazinyl]propanol (510 mg; 2.0 mmol) in toluene (40 ml) was refluxed for 16 h. The solvent was evaporated and the residue resuspended in ethyl acetate, filtered and evaporated to dryness. The residue was submitted to flash chromatography on silica gel 60 eluting with toluene/ethyl acetate (1:1). The product was taken up in ethanol, which was treated with hydrogen chloride in ether to give 200 mg of the title compound. M.p. 175°–176° C. MS (70 eV): m/z 479 (M+, 0.5%), 254 (49), 225 (88), 209 (100), 182 (34).

EXAMPLE 24

4-(2-Chlorophenyl)-1-(3-[3,4,5-trimethoxyphenyl(thiocarbamoyl)oxy]propyl)piperazine, hydrochloride A mixture of 3,4,5-trimethoxyphenylisothiocyanate (2.0 mmol) (produced as in Example 22) and 3-[4-(2-chlorophenyl) -1-piperazinyl]propanol (510 mg; 2.0 mmol) in toluene (40 ml) was refluxed for 16 h. The solvent was evaporated and the residue resuspended in ethyl acetate filtered and evaporated to dryness. The residue was submitted to flash chromatography on silica gel 60 eluting with toluene/ethyl acetate (1:1). The product was taken up in ethanol, which was treated with hydrogen chloride in ether to give 220 mg of the title compound. M.p. 182°–183° C. MS (70 eV): m/z 479 (M+, 0.5%), 254 (47), 225 (82), 209 (100), 182 (29).

EXAMPLE 25

4-(1-Naphthyl)-1-[3-(3,4-ethylenedioxyphenylcarbamoyloxy)propyl]piperazine, hydrochloride A mixture of 3,4-ethylenedioxyphenylisocyanate (2.0 mmol) (produced as in Example 16) and 3-[4-(1-naphthyl)-1-piperazinyl]propanol (540 mg; 2.0 mmol) in toluene (30 ml) was refluxed for 16 h. The reaction mixture was then concentrated and submitted to flash chromatography on silica gel 60 eluting with toluene graduated to toluene/ethyl acetate (1:3). The product was taken up in ethanol which was treated with hydrogen chloride in ether to give 650 mg of the title compound. M.p. 246°–248° C. MS (70 eV): m/z 447 (11%, M+), 270 (35), 225 (68), 177 (80), 154 (30), 141 (24), 127 (18), 121 (46), 93 (45), 70 (100).

EXAMPLE 26

4-[4-Bromo-1-naphthyl)-1-[3-(3,4-ethylenedioxyphenyl-carbamoyloxy)propyl]piperazine, hydrochloride A mixture of 3,4-ethylenedioxyphenylisocyanate (2.0 mmol) (produced as in Example 16) and 3-[4-(4-bromo-1-naphthyl)1-piperazinyl]propanol (700 mg; 20 mmol) in toluene (50 ml) was refluxed for 5 h. The reaction mixture was then concentrated and submitted to flash chromatography on silica gel 60 eluting with dichloromethane graduated to dichloromethane/ethyl acetate (1:1). The product was taken up in ethanol, which was treated with hydrogen chloride in ether to give 290 mg of the title compound. M.p. 233°–235° C. MS (70 eV): m/z 527 (1%, M+303 (10), 270 (31), 225 (61), 177 (100), 154 (28), 121 (48), 70 (43).

EXAMPLE 27

4-(4-Bromo-1-naphthyl)-1-[3-(3,4-methylenedioxy-phenylcarbamoyloxy)propyl]piperazine, hydrochloride A mixture of 3,4-methylenedioxyphenylisocyanate (330 mg; 2.0 mmol) (produced as in Example 13) and 3-[4-(4-bromo-1-naphthyl)-1-piperazinyl]propanol (700 mg; 2.0 mmol) in toluene (50 ml) was refluxed for 5 h. The reaction mixture was then concentrated and submitted to flash chromatography on silica gel 60 eluting with dichloromethane graduated to dichloromethane/ethyl acetate (1:1). The product was taken up in ethanol, which was treated with hydrogen chloride in ether to give 450 mg of the title compound. M.p. 219°–221° C. MS (70 eV): m/z 513 (3%, M+), 433 (28), 350 (11). 348 (11), 305 (16) 303 (17), 270 (38), 225 (62), 163 (100), 70 (62).

EXAMPLE 28

4-(1-Maphthyl)-1-(3-[3,4-ethylenedioxyphenyl(thiocarbamoyl)oxy]propyl)piperazine, hydrochloride A mixture of 3,4-ethylenedioxyphenylisothiocyanate (2.0 mmol) (produced as in example 11) and 3-[4-(1-naphthyl)-1-piperazinyl]propanol (240 mg; 2.0 mmol) in toluene (50 ml) was refluxed for 20 h. The solvent was evaporated and the residue resuspended in acetone filtered and evaporated to dryness. The residue was submitted to flash chromatography on silica gel 60 eluting with dichloromethane graduated to dichloromethane/ ethyl acetate (1:1). The product was taken up in ethanol, which was treated with hydrogen chloride in ether to give 50 mg of the title compound. M.p. 200°–201° C.

EXAMPLE 29

4-(1-Naphthyl)-1-[3-(1,2,3,4-tetrahydro-5-naphthylcarbamoyloxy)propyl]piperazine, hydrochloride A mixture of 5-amino-1,2,3,4-tetrahydronaphthalene (300 mg; 2.0 mmol) in toluene (10 ml) and phosgene (10 ml 20% in toluene) was refluxed for 6 h. The solvent was removed under reduced pressure to give crude 1,2,3,4-tetrahydronaphthyl -5-isocyanate. To the crude product was added 3-[4-(1-naphthyl)-1-piperazinyl]-propanol (240 mg; 2.0 mmol) in toluene (60 ml) and refluxed for 6 h. The reaction mixture was then concentrated and submitted to flash chromatography on silica gel 60 eluting with dichloromethane graduated to dichloromethane/ethyl acetate (1:1). The product was taken up in ethanol, which was treated with hydrogen chloride in ether to give 340 mg of the title compound. M.p. 227°–229° C. MS (70 eV): m/z 443 (M+,46), 270 (39), 225 (100), 173 (45), 145 (31), 127 (21), 114 (31), 70 (80).

EXAMPLE 30

1-[3-(3,4-Methylenedioxyphenylcarbamoyloxy)propyl]-4-(8quinolinyl)piperazine, hydrochloride A mixture of 3,4-methylenedioxyphenylisocyanate (330 mg; 2.0 mmol) (produced as in Example 13) and 3-[4-(8-quinolinyl) -1-piperazinyl]propanol (540 mg; 2.0 mmol) in toluene (50 ml) was refluxed for 2.5 h. The reaction mixture was then concentrated and submitted to flash chromatography on silica gel 60 eluting with dichloromethane graduated to dichloromethane/ethyl acetate (1:1). The product was taken up in ethanol, which was treated with hydrogen chloride in ether to give 740 mg of the title compound. M.p. 168°–170° C. MS 70 eV). m/z 434 (M+, 22%), 271 (27), 183 (23), 170 (32), 163 (45), 157 (100), 129 (42).

EXAMPLE 31

1-[3-(3,4-Ethylenedioxyphenylcarbamoyloxy)propyl]-4-(8-quinolinyl)piperazine, hydrochloride A mixture of 3,4-ethylenedioxyphenylisocyanate (2.0 mmol) (produced as in Example 16) and 3-[4-(8-quinolinyl)-1-piperazinyl]propanol (540 mg; 2.0 mmol) in toluene (50 ml) was refluxed for 4 h. The reaction mixture was then concentrated and submitted to flash chromatography on silica gel 60 eluting with dichloromethane graduated to dichloromethane/ethyl acetate (1:1). The product was taken up in ethanol, which was treated with hydrogen chloride in ether to give 730 mg of the title compound M.p. 144°–147° C. MS (70 eV): m/z 448 (M+, 10%), 271 (61), 183 (22), 177 (78), 170 (31). 157 (100). 129 (51).

EXAMPLE 32

1-[3-(3,4-Methylenedioxyphenylcarbamoyloxy)propyl]-4-(4quinolinyl)piperazine, hydrochloride A mixture of 3,4-methylenedioxyphenylisocyanate (330 mg; 2.0 mmol) (produced as in Example 13) and 3-[4-(5-quinolinyl) -1-piperazinyl]propanol (410 mg; 1.5 mmol) in toluene (50 ml) was refluxed for 4 h. The reaction mixture was then concentrated and submitted to flash chromatography on silica gel 60 eluting with dichloromethane graduated to dichloromethane/ethyl acetate (1:1). The product was taken up in ethanol, which was treated with hydrogen chloride in ether to give 110 mg of the title compound. M.p. 245°–246° C. MS (70 eV): m/z 434 (M+, 37%), 271 (65), 226 (100), 163 (70).

EXAMPLE 33

1-[3-(3,4-Ethylenedioxyphenylcarbamoyloxy)propyl]-4-(5quinolinyl)piperazine, hydrochloride A mixture of 3,4-ethylenedioxyphenylisocyanate (2.0 mmol) (produced as in Example 16) and 3-[4-(5-quinolinyl)-1-piperazinyl]propanol (410 mg; 1.5 mmol) in toluene (50 ml) was refluxed for 4 h. The reaction mixture was then concentrated and submitted to flash chromatography on silica gel 60 eluting with dichloromethane graduated to dichloromethane/ethyl acetate (1:1). The product was taken up in ethanol, which was treated with hydrogen chloride in ether to give 170 mg of the title compound. M.p. 237°–238° C. MS (70 eV): m/z 448 (M+, 14%), 271 (86), 226 (100), 177 (90).

EXAMPLE 34

1-(7-Methoxy-1-naphthyl)-4-[3-(3,4-methylenedioxyphenylcarbamoyloxy)propyl]piperazine, HCl A mixture of 3,4-methylenedioxyphenylisocyanate (330 mg; 2.0 mmol) (produced as in Example 13) and 3-[4-(7-methoxy-1-naphthyl)-piperazine-1-yl]propanol (0.6 g; 2 mmol) in toluene (60 ml) was refluxed for 1 h, concentrated and flash chromatographed on silica gel 60 eluting with toluene graduated to toluene/ethyl acetate (1:1). The product was taken up in ethanol, which was treated with hydrogen chloride in ether. Recrystallization from ethanol afforded 500 mg of the title compound. M.p. 236°–238° C. (dec.). MS (70 eV): m/z 463 (M+, 63%), 448 (9), 300 (100), 255 (54), 163 (68).

EXAMPLE 35

1-[3-(3,4-Ethylenedioxyphenylcarbamoyloxy)propyl]-4-(7-methoxy -1-naphthyl)piperazine, HCl A mixture of 3,4-ethylenedioxyphenylisocyanate (2.0 mmol; 350 mg) (produced as in Example 16) and 3-[4-(7-methoxy-1-naphthyl)piperazine-1-yl]propanol (0.6 g; 2.0 mmol) in toluene (60 ml) was refluxed for 1 h, concentrated, and flash chromatographed on silica gel 60 eluting with toluene graduated to toluene/ethyl acetate (1:1). The product was taken up in ethanol and precipitated as the hydrochloride by addition of hydrogen chloride in ether. Recrystallization from ethanol afforded 650 mg of the title compound. M.p. 250°–251° C. (dec.). MS (70 eV): m/z 477 (M+, 35%), 462 (8), 300 (56), 255 (85), 177 (100).

EXAMPLE 36

1-(1-Isoquinolinyl)-4-[3-(3,4-methylenedioxyphenylcarbamoyloxy)propyl]piperazine, HCl A mixture of 3,4-methylenedioxyphenylisocyanate (330 mg; 2.0 mmol) (produced as in Example 13) and 3-[4-(1-isoquinolinyl) piperazine-1-yl]propanol (0.54 g, 2 mmol) in toluene (60 ml) was stirred at room temperature for 16 h and then refluxed for 2 h. The mixture was concentrated in vacuo and taken up in a mixture of methylene chloride and aqueous potassium carbonate. The organic phase was dried over $Na_2SO_4$ and concentrated in vacuo. The product was dissolved in ethanol and treated with hydrogen chloride in ether precipitating the crude product. Trituration with ethanol gave the desired product as 750 mg white crystals M.p. 239°–240° C. MS (70 eV): m/z 434 (M+, 4%), 290 (22), 163 (27), 157 (100).

EXAMPLE 37

1-[3-(3,4-Ethylenedioxyphenylcarbamoyloxy)propyl]-4-(1isoquinolinyl)piperazine, HCl A mixture of 3,4-ethylenedioxyphenylisocyanate (0.35 g; 2 mmol) (produced as in Example 16) and 3-[4-(1-isoquinolinyl) piperazine-1-yl]propanol (0.54 g; 2 mmol) in toluene (60 ml) was stirred at room temperature for 16 h, refluxed for 2 h, and then concentrated in vacuo. The product was taken up in a mixture of methylene chloride and aqueous potassium carbonate. The organic phase was dried over $Na_2SO_4$ and evaporated. The product was dissolved in ethanol and precipitated as the hydrochloride by addition of hydrogen chloride in ether. Recrystallization from ethanol afforded 700 mg of the title compound. M.p. 222°–223° C. MS (70 eV): m/z 448 (M+, 3%), 304 (19), 177 (20), 157 (100), 127 (37).

EXAMPLE 38

1-[3-(6-Benzothiazolylcarbamoyloxy)propyl]-4-(8-quinolinyl)piperazine, HCl

A mixture of 6-benzothiazolylisothiocyanate (0.35 g; 2 mmol) (produced as in Example 19) and 3-[4-(8-quinolinyl)-piperazin -1-yl]propanol (0.54 g; 2 mmol) in toluene (60 ml) was refluxed for 6 h, and then concentrated in vacuo. The product was purified by column chromatography on silica gel 60 eluting with methylene chloride graduated to ethyl acetate. The product was taken up in ethanol and precipitated as the hydrochloride by addition of hydrogen chloride in ether. Recrystallization from ethanol (80%) afforded 470 mg of the title compound. M.p. 229°–230° C. MS (70 eV): m/z 477 (M+, 5%), 271 (32), 176 (70), 170 (26), 157 (100).

EXAMPLE 39

1-[3-(6-Benzothiazolylcarbamoyloxy)propyl]-4-(7-methoxy-1-naphthyl)piperazine, HCl A mixture of 6-benzothiazolylisothiocyanate (0.35 g; 2 mmol) (produced as in Example 19) and 3-[4-(7-methoxy-1-naphthyl) piperazin-1-yl]propanol (0.6 g; 2 mmol) in toluene (60 ml) was refluxed for 6 h. The reaction mixture was concentrated in vacuo and chromatographed through a column of silica gel 60 eluting with a gradient of methylene chloride to ethyl acetate. The product was dissolved in ethanol and hydrogen chloride in ether added to precipitate the desired product. Recrystallization from ethanol afforded 480 mg white crystals, M.p. 232°–233° C. MS (70 eV): m/z 476 (M+, 5%), 300 (65), 255 (50), 176 (100).

EXAMPLE 40

1-(8-Quinolinyl)-4-[3-3,4,5-trimethoxyphenylcarbamoyloxy) propyl]piperazine, oxalate A mixture of 3,4,5-trimethoxyphenylisocyanate (0.42 g; 2 mmol) (produced as in Example 1) and 3-[4-(8-quinolinyl)-piperazin -1-yl]propanol (0.54 g; 2 mmol) in toluene (50 ml) was refluxed for 10 h. The reaction mixture was concentrated in vacuo and chromatographed through a column of silica gel 60 eluting with methylene chloride graduated to ethyl acetate. The product was dissolved in ethanol and hydrogen chloride in ether added to precipitate the desired product. Recrystallization from aqueous ethanol and twice from acetone afforded 170 mg of the title compound. M.p. 190°–192° C. (dec.). MS (70 eV): m/z 480 (M+2%, 271 (23), 209 (47), 194 (52), 157 (100).

EXAMPLE 41

N-3-[4-(2-Chlorophenyl)piperazin-1-yl]propyl-N'-(3,4ethylenedioxyphenyl)urea, HCl A mixture of 3,4-methylenedioxyphenylisocyanate (0.18 g; mmol) (prepared as in Example 13) and 3-[4-(2-chlorophenyl) piperazin-1-yl]propylamine (0.2 g; 0.8 mmol) in toluene (60 ml) was refluxed for 0.5 h. The reaction mixture was concentrated in vacuo and then purified by column chromatography on silica gel 60 eluting with ethyl acetate graduated to ethyl acetate/methanol (1:1). The product was dissolved in ethanol and hydrogen chloride in ether added to precipitate the title compound. Recrystallization from ethanol/ether gave 70 mg white crystals. M.p. 217°-219° C. MS (70 eV): m/z 432/430 (M+, 1%, 3%), 280 (20), 209 (36), 177 (100), 166 (15), 151 (80).

EXAMPLE 42

N-3-[4-(2-Chlorophenyl)piperazin-1-yl]propyl-N'-3,4-ethyl-enedioxyphenyl -N''-methylguanidine, oxalate A mixture of N-3-[4-(2-chlorophenyl)piperazin-1-yl]propyl-N '-(3,4-ethylenedioxyphenyl)thiourea of Example 11 (1.35 g; 3 mmol), triphenylphosphin (1.02 g; 3.9 mmol), carbon tetrachloride (0.56 ml), triethylamine (0.3 g; 3 mmol) and methylene chloride (15 ml) Was stirred at reflux for 3 h and at 400° C. for 16 h. The reaction mixture was concentrated in vacuo and then taken up in petroleum ether. The solution was filtered and concentrated in vacuo to give 0.7 g N-3-[4-(2-chlorophenyl)piperazin-1-yl]propyl-N'-(3,4-ethylenedioxyphenyl)carbodiimide as an oil.

To this compound (0.35 g; 0.77 mmol) in pyridine (0.7 ml) was added methylamine, HCl (57 mg). The mixture was stirred at 30° C. for 16 h, diluted with water and filtered. The filtrate was extracted with methylene chloride. The organic phase was evaporated, and the resulting oil dissolved in acetone. Addition of oxalic acid (150 mg) in acetone (2 ml) afforded the title compound. Recrystallization from isopropanol gave 100 mg white crystals. M.p. 78°-80° C. (dec.). MS (70 eV): m/z: 443 (M+, 13%), 293 (10), 277 (80), 249 (15), 234 (17), 221 (32), 164 (60), 151 (72), 44 (100).

We claim:

1. A compound of formula I

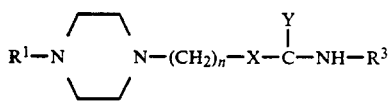

wherein
$R^1$ is a phenyl group which is substituted with halogen or perhalomethyl;
n is 1, 2, 3 or 4;
X is —O— or

wherein $R^2$ is hydrogen, $C_{1-6}$-alkyl or $C_{3-8}$-cycloalkyl;
Y is =O, =S, or =NZ wherein Z is hydrogen, $C_{1-6}$-alkyl or CN;
$R^3$ is

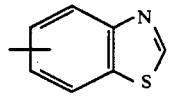

or a physiologically acceptable salt thereof or an optical isomer thereof.

2. The compound according to claim 1 which is 4-(4-chlorophenyl)-1-[3-(6-benzothiazolylcarbamoyloxy)-propyl]piperazine; or a physiologically acceptable salt thereof or an optical isomer thereof.

3. A compound of formula I

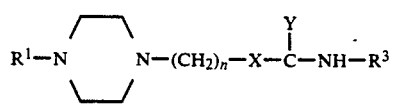

wherein
$R^1$ is a phenyl group which is substituted with halogen or perhalomethyl;
n is 3;
X is —O— or

wherein $R^2$ is hydrogen, $C_{1-6}$-alkyl or $C_{3-8}$-cycloalkyl;
Y is =S;
$R^3$ is

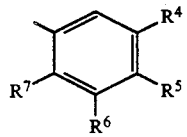

wherein $R^4$, $R^5$, $R^6$ and $R^7$, which may be identical or different, are hydrogen, alkyl, halogen, $C_{1-6}$-alkoxy, perhalomethyl, provided that $R^4$, $R^5$, $R^6$ and $R^7$ are not each hydrogen; or a physiologically acceptable salt thereof or an optical isomer thereof.

4. The compound according to claim 3 which is 4-(4-chlorophenyl)-1-[3-(3,4,5-trimethoxyphenyl (thiocarbamoyl)oxy)propyl]piperazine;
4-(3-chlorophenyl)-1[3-(3,4,5-trimethoxyphenyl (thiocarbamoyl)oxy)propyl]piperazine;
4-(2-chlorophenyl)-1[3-(3,4,5-trimethoxyphenyl (thiocarbamoyl)oxy)propyl]piperazine; or a physiologically acceptable salt thereof or an optical isomer thereof.

5. A compound which is
4-(4-chlorophenyl)-1-[3-(3,4,5-trimethoxyphenylcarbamoyloxy) propyl]piperazine;
4-(2-chlorophenyl)-1-[3-(3,4,5-trimethoxyphenylcarbamoyloxy) propyl]piperazine;
4-(4-chlorophenyl)-1-[3-(3,4,5-trimethoxyphenylcarbamoyloxy) propyl]piperazine; or a physiologically acceptable salt thereof or an optical isomer thereof.

6. A compound which is
4-(3-chlorophenyl)-1-[3-(3,4,-methylenedioxyphenylcarbamoyloxy) propyl]piperazine;
4-(4-chlorophenyl)-1-[3-(3,4,-ethylenedioxyphenylcarbamoyloxy) propyl]piperazine;
4-(3-chlorophenyl)-1-[3-(3,4,-ethylenedioxyphenylcarbamoyloxy) propyl]piperazine;
N-3-(4-(2-chlorophenyl)piperazin-1-yl]propyl-N$^1$-3,4-ethylenedioxyphenyl)thiourea; or a physiologically acceptable salt thereof or an optical isomer thereof.

7. A pharmaceutical composition for use in treating a central nervous system ailment related to the 5-HT$_2$ receptor system comprising an effective amount of a compound according to claim 1 and a pharmaceutically acceptable carrier or diluent.

8. A pharmaceutical composition for use in treating a central nervous system ailment related to the 5-HT$_2$ receptor system comprising an effective amount of a compound according to claim 3 and a pharmaceutically acceptable carrier or diluent.

9. A pharmaceutical composition for use in treating a central nervous system ailment related to the 5-HT$_2$ receptor system comprising an effective amount of a compound according to claim 5 and a pharmaceutically acceptable carrier or diluent.

10. A pharmaceutical composition for use in treating a central nervous system ailment related to the 5-HT$_2$ receptor system comprising an effective amount of a compound according to claim 6 and a pharmaceutically acceptable carrier or diluent.

11. A method of treating a central nervous system ailment related to the 5-HT$_2$ receptor system in a subject in need thereof comprising administering an effective amount of a compound of claim 1.

12. A method of treating a central nervous system ailment related to the 5-HT$_2$ receptor system in a subject in need thereof comprising administering an effective amount of a compound of claim 3.

13. A method of treating a central nervous system ailment related to the 5-HT$_2$ receptor system in a subject in need thereof comprising administering an effective amount of a compound of claim 5.

14. A method of treating a central nervous system ailment related to the 5-HT$_2$ receptor system in a subject in need thereof comprising administering an effective amount of a compound of claim 6.

15. A method of treating a central nervous system ailment related to the 5-HT$_2$ receptor system in a subject in need thereof comprising administering an effective amount of a compound of claim 7.

16. A method of treating a central nervous system ailment related to the 5-HT$_2$ receptor system in a subject in need thereof comprising administering an effective amount of a compound of claim 8.

17. A method of treating a central nervous system ailment related to the 5-HT$_2$ receptor system in a subject in need thereof comprising administering an effective amount of a compound of claim 9.

18. A method of treating a central nervous system ailment related to the 5-HT$_2$ receptor system in a subject in need thereof comprising administering an effective amount of a compound of claim 10.

19. A compound of formula I $$R^1-N\diagup\!\!\!\diagdown N-(CH_2)_n-X-\overset{Y}{\underset{|}{C}}-NH-R^3 \quad (I)$$

wherein
R$^1$ is a quinolinyl or isoquinolinyl group which may be substituted with C$_{1-6}$-alkyl, C$_{3-8}$-cycloalkyl, C$_{1-6}$-alkoxy, halogen, cyano, nitro or perhalomethyl;
n is 1, 2, 3 or 4;
X is —O— or $$-\underset{\underset{R^2}{|}}{N}-$$

wherein R$^2$ is hydrogen, C$_{1-6}$-alkyl or C$_{3-8}$-cycloalkyl;
Y is =O, =S, or =NZ wherein Z is hydrogen, C$_{1-6}$-alkyl or CN; and
R$^3$ is selected from the groups consisting of

[benzothiazole] or [substituted benzene with R$^4$, R$^5$, R$^6$, R$^7$]

wherein R$^4$, R$^5$, R$^6$ and R$^7$, which may be identical or different, are hydrogen, alkyl, halogen, C$_{1-6}$-alkoxy, perhalomethyl; or R$^6$ and R$^7$ are hydrogen and R$^4$ and R$^5$ form the following ring

[dioxy ring with (CH$_2$)$_{n'}$]

wherein n' is 1, 2 or 3; or R$^4$ and R$^5$ are hydrogen and R$^6$ and R$^7$ together are —(CH$_2$)$_{n''}$—wherein n'' is 3, 4 or 5, provided that R$^4$, R$^5$, R$^6$ and R$^7$ are not each hydrogen; or a physiologically acceptable salt thereof or an optical isomer thereof.

20. A compound which is
4-(1-naphthyl)-1-[3-(3,4-methylenedioxyphenylcarbamoyloxy)propyl]piperazine;
4-(1-naphthyl)-1-[3-(3,4-ethylenedioxyphenylcarbamoyloxy)propyl]piperazine;
4-(4-bromo-1-naphthyl)-1-[3-(3,4-ethylenedioxyphenylcarbamoyloxy)propyl]piperazine;
4-(4-bromo-1-naphthyl)-1-[3-(3,4-methylenedioxyphenylcarbamoyloxy)propyl]piperazine;
4-(1-naphthyl)-1-[3-(3,4-ethylenedioxyphenyl(thiocarbamoyl)oxy)propyl]piperazine;
4-(1-naphthyl)-1-[3-(1,2,3,4-tetrahydro-5-naphthylcarbamoyloxy)propyl]piperazine;
4-(8-quinolinyl)-1-[3-(3,4-methylenedioxyphenylcarbamoyloxy) propyl]piperazine; or a physiologically acceptable salt thereof or an optical isomer thereof.

21. A pharmaceutical composition for use in treating a central nervous system ailment related to the 5-HT$_2$ receptor system comprising an effective amount of a compound according to claim 19 and a pharmaceutically acceptable carrier or diluent.

22. A pharmaceutical composition for use in treating a central nervous system ailment related to the 5-HT$_2$ receptor system comprising an effective amount of a compound according to claim 20 and a pharmaceutically acceptable carrier or diluent.

23. The pharmaceutical composition according to claim 7, 8, 9, 10, 21 or 22 which contains between 0.1 mg and 250 mg of the active ingredient per dose unit.

24. A method of treating a central nervous system ailment related to the 5-HT$_2$ receptor system in a subject in need thereof comprising administering an effective amount of a compound of claim 19.

25. A method of treating a central nervous system ailment related to the 5-HT$_2$ receptor system in a subject in need thereof comprising administering an effective amount of a compound of claim 20.

26. A method of treating a central nervous system ailment related to the 5-HT$_2$ receptor system in a subject in need thereof comprising administering an effective amount of a compound of claim 21.

27. A method of treating a central nervous system ailment related to the 5-HT$_2$ receptor system in a subject in need thereof comprising administering an effective amount of a compound of claim 22.

* * * * *